US012708791B2

(12) United States Patent
Whelan et al.

(10) Patent No.: US 12,708,791 B2
(45) Date of Patent: Aug. 18, 2026

(54) MANAGEMENT OF DERMAL NEUROFIBROMATOSIS LESIONS

(71) Applicant: Sun Pharmaceutical Industries, Inc., Princeton, NJ (US)

(72) Inventors: Harry Thomas Whelan, Whitefish Bay, WI (US); Brendan John Quirk, Mayville, WI (US); Edit Olasz Harken, Pewaukee, WI (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 604 days.

(21) Appl. No.: 17/913,741

(22) PCT Filed: Mar. 26, 2021

(86) PCT No.: PCT/IB2021/052535

§ 371 (c)(1),
(2) Date: Sep. 22, 2022

(87) PCT Pub. No.: WO2021/191865

PCT Pub. Date: Sep. 30, 2021

(65) Prior Publication Data

US 2023/0035733 A1 Feb. 2, 2023

Related U.S. Application Data

(60) Provisional application No. 63/000,317, filed on Mar. 26, 2020.

(51) Int. Cl.
*A61N 5/06* (2006.01)
*A61P 35/00* (2006.01)

(52) U.S. Cl.
CPC ........... *A61N 5/062* (2013.01); *A61N 5/0616* (2013.01); *A61P 35/00* (2018.01); *A61N 2005/0651* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 6,223,071 | B1 | 4/2001 | Lundahl et al. |
| 6,709,446 | B2 | 3/2004 | Lundahl et al. |

(Continued)

FOREIGN PATENT DOCUMENTS

| | | | |
|---|---|---|---|
| WO | WO-2013/120497 A1 | 8/2013 | |
| WO | WO-2017/066270 A1 | 4/2017 | |

OTHER PUBLICATIONS

Gupta et al (Gupta, J. Ryder, "Photodynamic Therapy and Topical Aminolevulinic Acid," Am. J. Clin. Derm. 4, 699-708 (issued Oct. 2003), as published Aug. 21, 2012.*

(Continued)

*Primary Examiner* — Mallika D Fairchild
(74) *Attorney, Agent, or Firm* — Foley & Lardner LLP

(57) ABSTRACT

Dermal neurofibroma, in particular Neurofibromatosis Type I (NF1) leads to progressive tumor proliferation with no known mechanism to inhibit growth. The present invention relates to the use of photodynamic therapy (PDT) for attenuating tumor growth in NF1 patients. More particularly the invention provides a method of treating dermal neurofibroma comprising topically applying a pharmaceutical composition comprising a photosensitizer to the affected area of a patient, incubating the affected area, and irradiating the affected area with a light of suitable wavelength as per the photosensitizer used, wherein the treatment is characterized by inhibiting the progression of tumor growth and/or reduction in tumor size and/or increased mortality rate of the neurofibroma cell.

10 Claims, 8 Drawing Sheets

(56) References Cited

U.S. PATENT DOCUMENTS

| | | | | |
|---|---|---|---|---|
| 7,190,109 | B2 | 3/2007 | Lundahl et al. | |
| 7,723,910 | B2 | 5/2010 | Lundahl et al. | |
| 8,030,836 | B2 | 10/2011 | Lundahl et al. | |
| 8,216,289 | B2 | 7/2012 | Lundahl et al. | |
| 8,758,418 | B2 | 6/2014 | Lundahl et al. | |
| 2004/0266989 | A1 | 12/2004 | Currie et al. | |
| 2006/0251668 | A1 | 11/2006 | Goletz et al. | |
| 2009/0118240 | A1 * | 5/2009 | Chen | A61K 31/661 514/567 |
| 2009/0214560 | A1 | 8/2009 | Min et al. | |
| 2015/0216830 | A1 | 8/2015 | Rephaeli et al. | |
| 2016/0082241 | A1 * | 3/2016 | Burton | A61M 5/322 604/173 |
| 2017/0304654 | A1 * | 10/2017 | Blanche | A61B 18/18 |

OTHER PUBLICATIONS

B. Quirk, E. Olasz, S. Kumar, D. Basel, H. Whelan, "Photodynamic Therapy for Benign Cutaneous Neurofibromas Using Aminolevulinic Acid Topical Application and 633 nm Red Light Illumination," Photobiomodulation, Photomedicine, and Laser Surg., Jun. 2021; 39(6):411-417, published online Jan. 18, 2021.

S. Frustaci et al., Adjuvant chemotherapy for adult soft tissue sarcomas of the extremities and girdles: results of the Italian randomized cooperative trial, J Clin. Oncol, Mar. 2001; 19: 1238-47.

A. Gupta, J. Ryder, "Photodynamic Therapy and Topical Aminolevulinic Acid," Am. J. Clin. Derm. 4, 699-708 (issued Oct. 2003), as published Aug. 21, 2012.

S. Huson et al., Von Recklinghausen neurofibromatosis: a clinical and population study in south-east Wales, Brain Dec. 1988; 111: 1355-81.

M. Lammert, J. Friedman, L. Kluwe, V. Mautner, Prevalence of Neurofibromatosis 1 in German Children at Elementary School Enrollment, Arch. Dermatol. Jan. 2005; 141: 71-74.

Phase I Photodynamic Therapy (PDT) for Benign Dermal Neurofibromas (NF1), H. Whelan, NCT01682811, ClinicalTrials.gov, Sep. 11, 2012, Results posted Jun. 18, 2021, accessible via https://clinicaltrials.gov/ct2/show/NCT01682811 (last accessed Aug. 27, 2022) (24 pages).

Sarcoma Meta-analysis Collaboration (SMAC), Adjuvant chemotherapy for localised resectable soft tissue sarcoma in adults, Cochrane Database Syst Rev 2000; 4: CD001419.

V. Riccardi, B. Quirk, E. Olasz, S. Kumar, D. Basel, H. Whelan, "Photodynamic Therapy for Benign Dermal Neurofibromas," Children's Tumor Foundation conference material, May 2019 (1 page).

David H. Gutmann et al., The Diagnostic Evaluation and Multidisciplinary Management of Neurofibromatosis 1 and Neurofibromatosis 2, J.A.M.A., vol. 278, No. 1, Jul. 2, 1997, pp. 51-57.

International Preliminary Report on Patentability and Written Opinion, International Application No. PCT/IB2021/052535, Report issued Sep. 22, 2022 (6 pages).

* cited by examiner

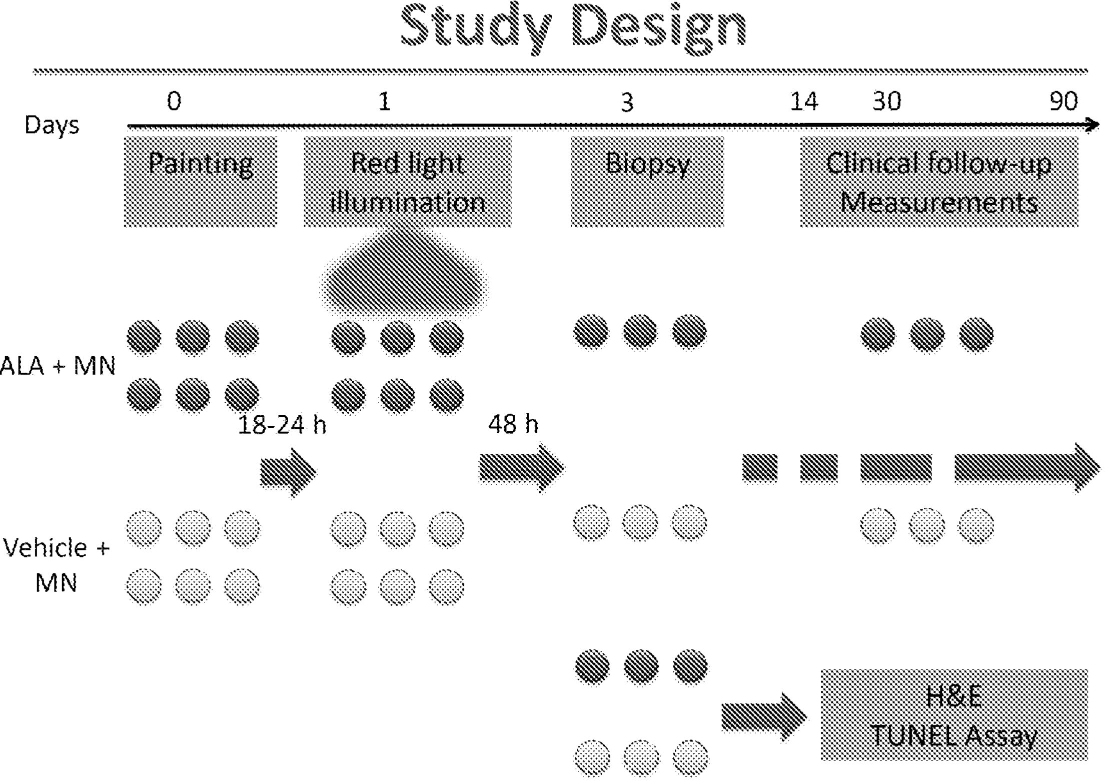
Figure 1: Schematic of the study design

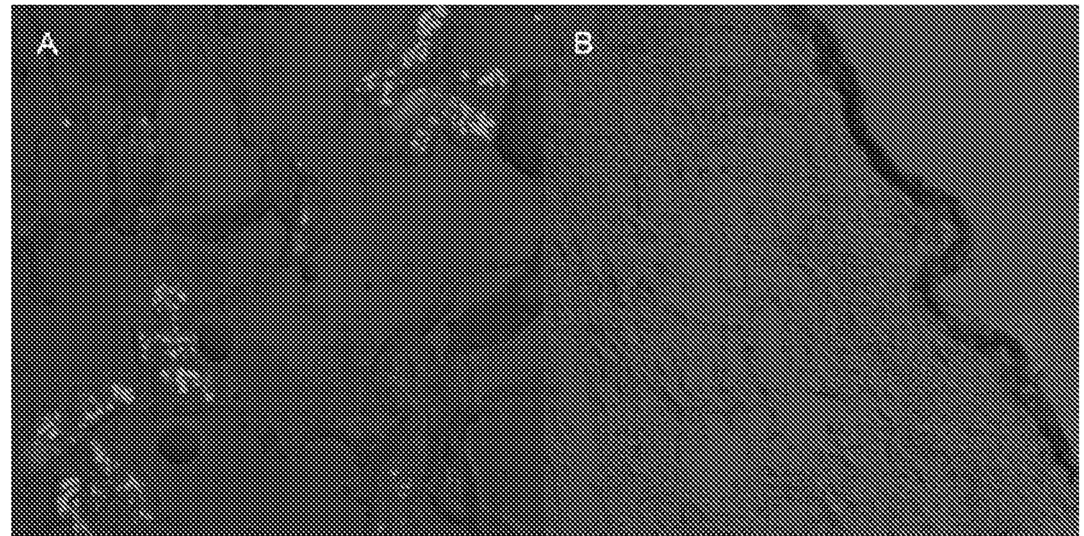
Figure 2: Confocal microscope fluorescence imaging (200X).
a) Tumor tissue treated with MN and ALA.
b) Tumor tissue treated with MN and vehicle only

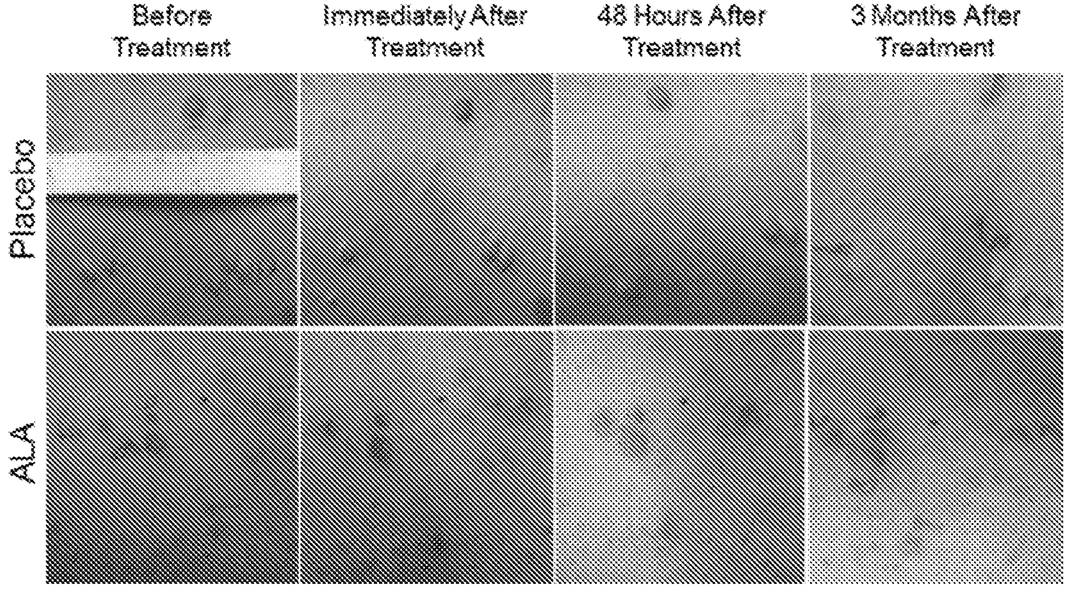
Figure 3: NF1 lesions before and after 633 nm red light treatment. Top row placebo (vehicle only) lesions; bottom row ALA-treated lesions. 127 x 70mm (300 x 300 DPI)

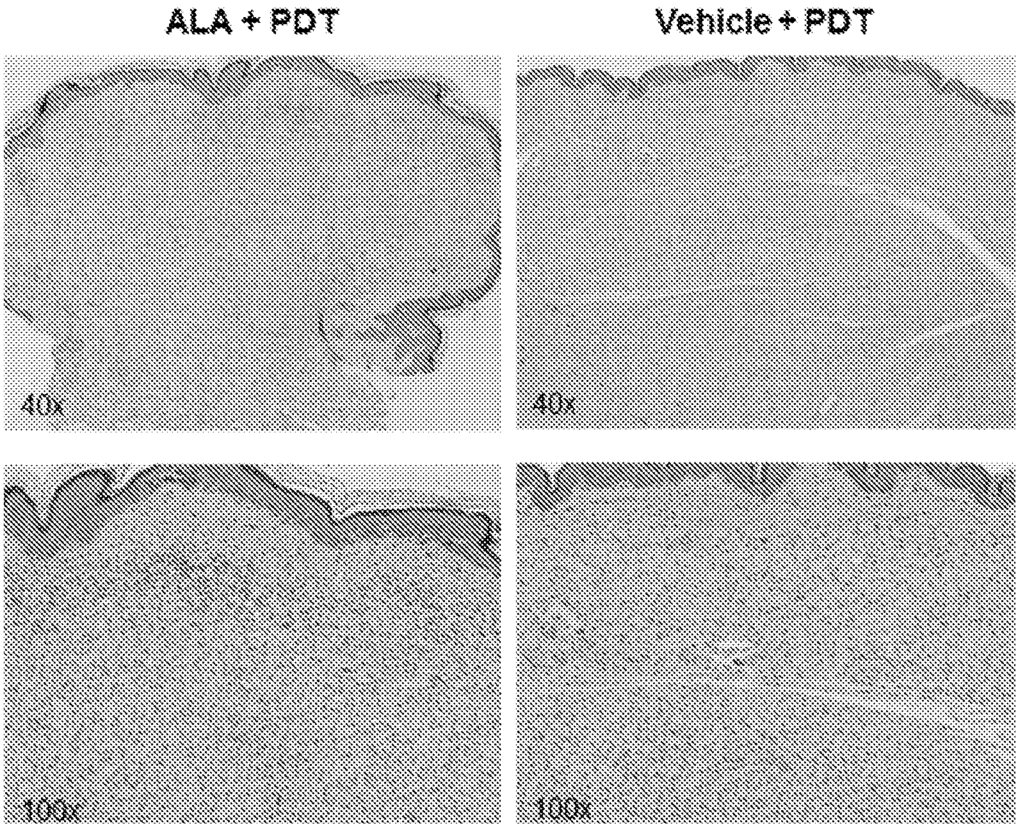
Figure 4: Light microscopic exam of NF1 lesion tissue samples using H&E staining. Top row 40X; bottom row 100X 127x106mm (300 x 300 DPI)

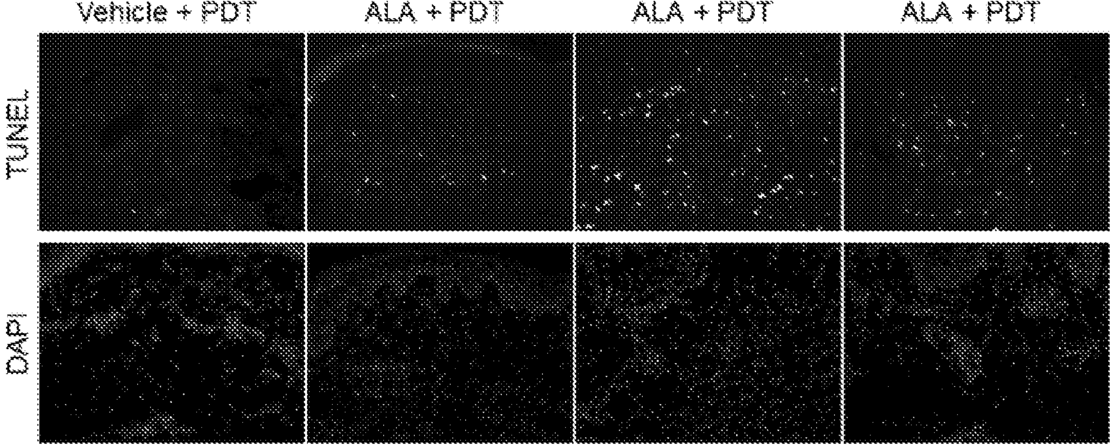
Figure 5: Fluorescent microscope imaging of NF1 lesion tissue samples 100X (vertical sections). Top row TUNEL (terminal deoxynucleotidyl transferase dUTP nick end labeling) staining; bottom row DAPI (4′,6-diamidino-2-phenylindole) staining 127 x 63mm (300 x 300 DPI)

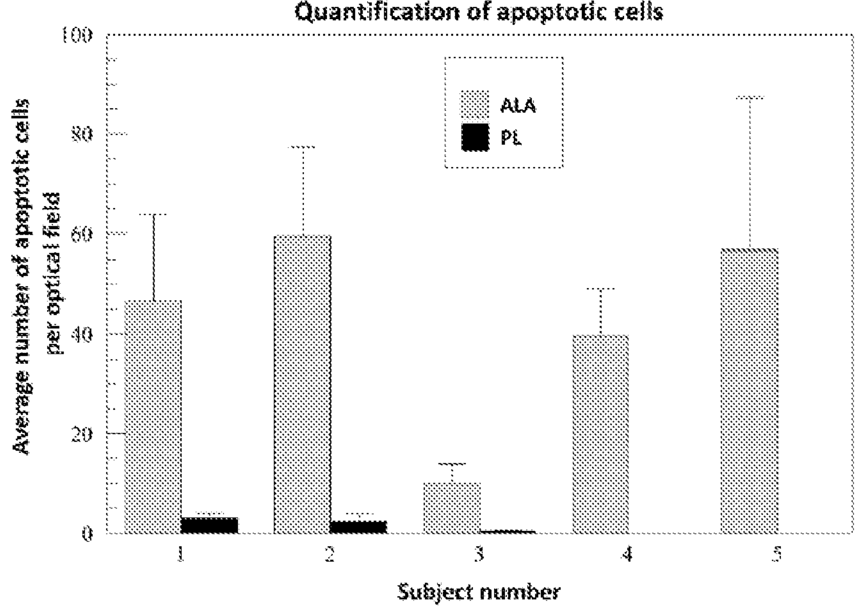
Figure 6: Quantification of apoptotic cells as determined by TUNEL Assay. Individual results; ALA- and placebo- treated lesions 1381x1067mm (120 x 120 DPI)

Figure 7:
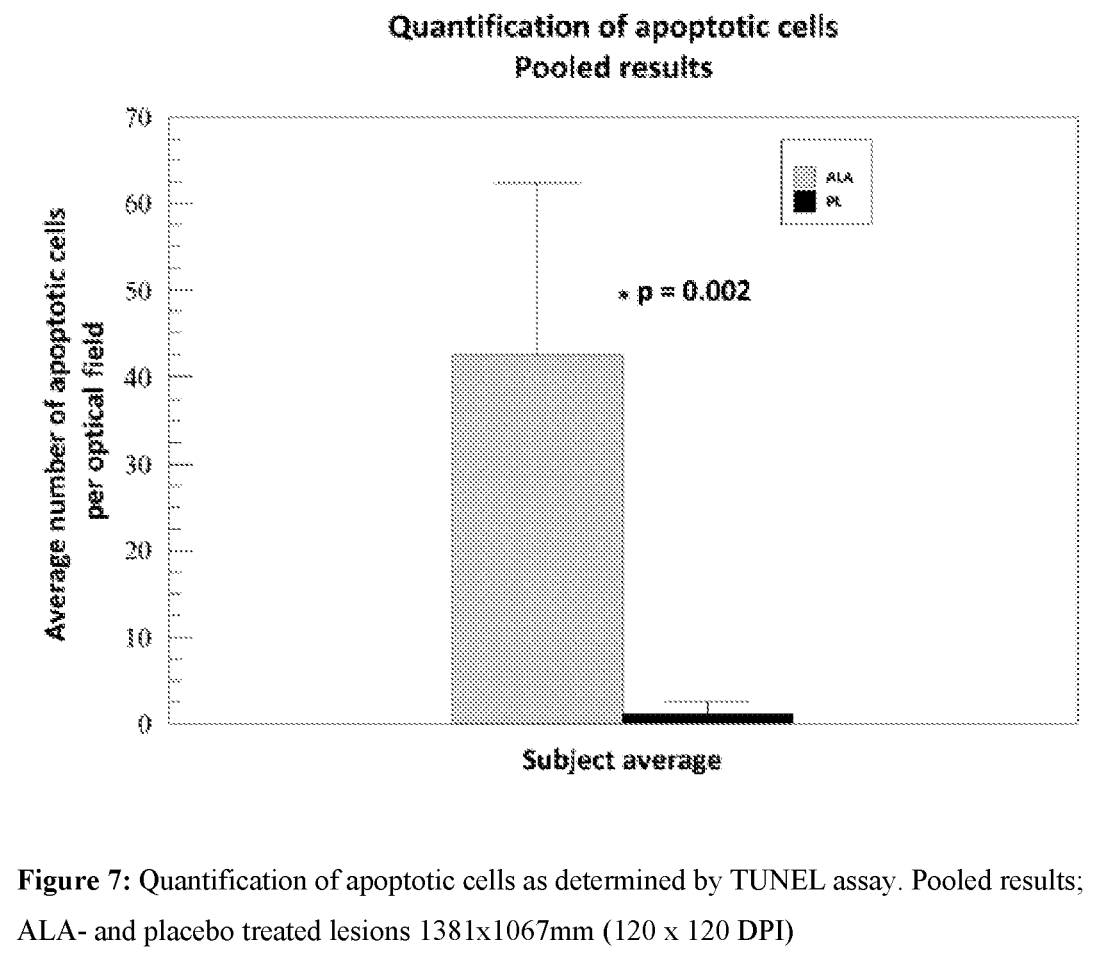

Quantification of apoptotic cells
Pooled results 70
60
50
40
30
20
10
0

Average number of apoptotic cells per optical field

ALA
PL

* p = 0.002

Subject average

Figure 7: Quantification of apoptotic cells as determined by TUNEL assay. Pooled results; ALA- and placebo treated lesions 1381x1067mm (120 x 120 DPI)

MANAGEMENT OF DERMAL NEUROFIBROMATOSIS LESIONS

CROSS-REFERENCE TO RELATED APPLICATIONS

The present application is a U.S. national stage entry of International Application No. PCT/IB2021/052535 filed Mar. 26, 2021, which claims priority to U.S. Provisional Application No. 63/000,317 filed Mar. 26, 2020, the entire contents of each of which are incorporated herein by reference.

BACKGROUND OF THE INVENTION

Neurofibromatosis Type I (NF1) is an autosomal dominant disease, first described by Frederich von Recklinghausen in 1882. NF1 is a tumor suppressor gene and shows variable expressivity; a tumorous condition is caused due to the loss and/or mutation of the NF1 gene which leads to a chronic multisystem disorder affecting many different tissues. It is associated with the development of dermal and plexiform neurofibromas. It is said to affect about one in 2500 to one in 3000 people worldwide and can be benign and malignant (Lammert M, Friedman J M, Kluwe L, Mautner V F, Prevalence of neurofibromatosis 1 in German children at elementary school enrollment. Arch Dermatol 2005; 141: 71-74; Husandon S M, Harper P S, Compston D A, Von Recklinghausen neurofibromatosis: a clinical and population study in south-east Wales, Brain 1988; 111: 1355-81). Benign tumors are one of the common findings in such patients with localized overgrowth of neural-crest-derived tissue. In adolescence and adulthood, dermal neurofibromas exhibit as small tumors involving the terminal nerve fibers.

Of the two types, benign neurofibromas can be cutaneous, subcutaneous or nodular.

Intra-cutaneous neurofibromas develop during late childhood or early adolescence and do not undergo malignant transformation. These tumors might cause local pruritus. Intra-cutaneous neurofibromas can result in disfigurement with hundreds or thousands of these neurofibromas in a patient. Although tumors can be removed by a plastic surgeon, spinal neurofibromas can occur at single or multiple nerve roots causing sensory and motor deficits. Although neurofibromas are commonly found on the skin but can also be located deep within the body. It increases with age deepening the clinical symptoms. In these patients, tumor removal should be led by symptoms—such as pain and functional deficits and findings of a risk-benefit assessment. The second type, that is, plexiform neurofibromas which arise from multiple nerve fascicles and can grow along the length of a nerve. Plexiform neurofibromas develop in about 30-50% of individuals with NF1. It typically manifests at birth but can continue to grow during adolescence and early adulthood. These tumors enlarge most prominently during the first decade of life.

These tumors can also extend into surrounding structures, causing substantial pain and bone destruction.

Many patients with NF1 are often at risk of developing cancers such as gliomas, neurofibromas and malignant peripheral nerve sheath tumors (MPNSTs). There are varying features and clinical heterogeneity inherent to this disorder, patients can present to different medical and surgical specialists. Prompt diagnosis and optimum care along with awareness of the diverse clinical features of this disorder is required. Current treatment options are surgical, if necessary. Multidisciplinary approach to care is advocated entailing diverse specialists throughout the lifetime. Tumors that develop in patients with neurofibromatosis type 1 are heterogeneous therefore represent complex tumors in with distinct cell types and growth-control pathways regulate tumor behaviour. Due to cell-specific complexities of RAS signaling, therapeutic approaches for NF1 will likely have to focus on a particular tissue and manifestation of the disease.

Photodynamic Therapy (PDT) or Radiation therapy (RT) is used to treat neurofibromatosis lesions. It could delay time to recurrence. Use of adjuvant chemotherapy is controversial (Frustaci S, Gherlinzoni F, De Paoli A, et al., Adjuvant chemotherapy for adult soft tissue sarcomas of the extremities and girdles: results of the Italian randomized cooperative trial, J Clin Oncol 2001; 19: 1238-47; Sarcoma Meta-analysis Collaboration (SMAC), Adjuvant chemotherapy for localised resectable soft tissue sarcoma in adults, Cochrane Database Syst Rev 2000; 4: CD001419.) PDT for use in treating neurofibromatosis lesions is also significant as pathogenesis, clinical spectrum, and natural history of these anomalies remains poorly understood; and the only known factor pointing towards impaired NF1 gene function in vascular endothelial cells, results in increased proliferation and growth of tumor cells. This relies on photoreaction caused by use photosensitizers (PS) and light to generate reactive oxygen species, which can interact with biomolecules and subcellular organelles to interrupt key molecular functions and ultimately causing cell death and destruction of tissues.

No known medical therapies that are beneficial to patients with NF1 are available. Several drug trials have been initiated, looking for medications that slow or halt the growth of neurofibromas. Thus far, none of these medications has demonstrated significant benefit, though various research trials involving chemotherapeutic and other agents are under way, in an attempt to slow the growth of plexiform neurofibromas. There are no therapies proven to be beneficial in decreasing neurofibroma burden in patients with NF1. The present invention provides a method of treating dermal neurofibromas by use of photodynamic therapy after topical application of 5-aminolevulinic acid (ALA) on the affected area of skin. ALA is a pro-drug that needs conversion, it is mitochondrial metabolite that is the first step in heme synthesis. ALA can be activated with blue light. Wavelength of light, as mentioned herein after, is known in the art and is not limited by examples. Blue light activation can be in the range 410 nm for superficial lesions, or longer wavelength (630 nm range) red photosensitization for deeper penetration.

Therefore, following application of ALA, ALA is absorbed and gets metabolically converted to protoporphyrin IX (PpIX), which subsequently accumulates in metabolically active cells. When exposed to appropriate light energy, the accumulated PpIX produces a cytotoxic photodynamic reaction light (630 nm range) for deeper infiltration. Phase I light-dose escalation study was conducted to determine safety and adverse effects of PDT treatment of cutaneous neurofibromas (cNF).

SUMMARY OF THE INVENTION

The invention relates to use of photodynamic therapy for treatment of dermal neurofibroma. The invention further relates to a method of treating dermal neurofibroma comprising:

a. topically applying a pharmaceutical composition comprising a photosensitizer to the affected area of a patient, incubating the affected area, and
b. irradiating the affected area with a light of suitable wavelength as per the photosensitizer used.

Such photodynamic therapy of dermal neurofibroma may result in the inhibition of the progression of tumor growth and/or reduction in tumor size and/or increased mortality rate of the neurofibroma cells.

The invention may further comprise an additional step of microneedling before and/or after topical application of the photosensitizer composition.

DESCRIPTION OF THE FIGURES

FIG. 1: Schematic of the study design.

FIG. 2*a*: Comparison of fluorescence between ALA Treated tissue sample and normal tissues.

FIG. 2*b*: Control and vehicle only tumors showing no visible fluorescence.

FIG. 3: Red light erythema and edema around ALA-treated (n=24) but not placebo (n=20) lesions.

FIG. 4: Light microscopy exam showing mixed infiltrate in ALA-treated but not vehicle-treated tumors or normal adjacent tissue.

FIG. 5: TUNEL evaluated tumor samples average number of apoptotic cells per visual field.

FIG. 6: Apoptotic cells in the ALA-treated Dermatofibroma (DF) samples compared to the vehicle-treated samples.

FIG. 7: Quantification of apoptotic cells as determined by TUNEL assay.

DETAILED DESCRIPTION OF THE INVENTION

Figure 8:
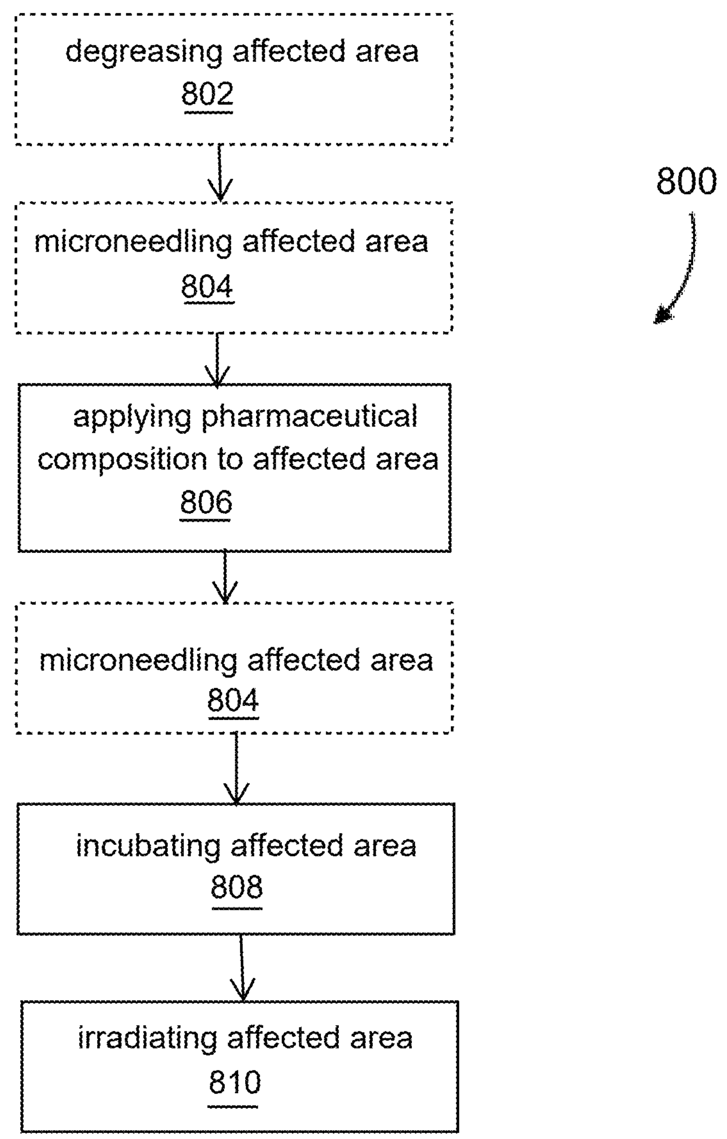
FIG. 8: Process flow diagram depicting an exemplary method of treating dermal neurofibroma according to an embodiment.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The following terms are used throughout and are as defined below.

As used herein and in the appended claims, singular articles such as "a" and "an" and "the" and similar references in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illustrate the embodiments and does not pose a limitation on the scope of the claims unless otherwise stated. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The expression "comprising" means "including, but not limited to." Thus, other non-mentioned substances, additives, devices or steps may be present. Unless otherwise specified, "a" or "an" means one or more.

Unless otherwise indicated, all numbers expressing quantities of properties, parameters, conditions, and so forth, used in the specification and claims are to be understood as being modified in all instances by the term "about." Accordingly, unless indicated to the contrary, the numerical parameters set forth in the following specification and attached claims are approximations. Any numerical parameter should at least be construed in light of the number reported significant digits and by applying ordinary rounding techniques. The term "about" when used before a numerical designation, e.g., temperature, time, amount, and concentration including range, indicates approximations which may vary by (+) or (—) 10%, 5% or 1%.

As will be understood by one of skill in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

"Neurofibroma" or "NF1" refers to autosomal-dominant genetically inherited disease of Schwann cells, fibroblasts, perineural cells, and/or mast cells in a variably myxoid background. It is benign nerve-sheath tumor in the peripheral nervous system. Neurofibromas are found as standalone tumors or with neurofibromatosis type I (NF1). Neurofibromas have been subdivided into two broad categories: dermal and plexiform. According to the World Health Organization classification system, dermal and plexiform neurofibromas are grade I tumors.

Dermal neurofibromas or Cutaneous neurofibromas are associated with a single peripheral nerve, while plexiform neurofibromas with multiple nerve bundles. Dermal neurofibromas originate in nerves in the skin. Three kinds are distinguished as: (1) Discrete cutaneous neurofibromas which are sessile or pedunculated masses on skin, fleshy and non-tender, and can vary in size (2) Discrete subcutaneous neurofibroma which look like bumps on the skin and can sometimes be tender (3) Deep nodular neurofibromas which involving tissues and organs underneath the dermis, but otherwise resembling cutaneous and subcutaneous neurofibromas. Dermal neurofibromas or Cutaneous neurofibromas will be used interchangeably herein.

"Photodynamic Therapy (PDT)" is a form of phototherapy involving light and a photosensitizing chemical substance, used in conjunction with molecular oxygen to elicit cell death (phototoxicity). PDT is a multi-stage process and involve at least two components: a photosensitizer and a light source that can generate a light of particular wavelength according to the photosensitizer used.

"Photosensitizer" is a chemical compound that is promoted to an excited state upon absorption of light. It undergoes intersystem crossing (ISC) with oxygen to produce singlet oxygen. This species is highly cytotoxic, rapidly attacking any organic compounds it encounters. It is rapidly eliminated from cells. When a photosensitizer is in its excited state, it can interact with molecular triplet oxygen ($^3O_2$) and produce radicals and reactive oxygen species (ROS), crucial to the Type II mechanism. These species include singlet oxygen ($^1O_2$), hydroxyl radicals (•OH) and superoxide ($O_2$−) ions. They can interact with cellular components including unsaturated lipids, amino acid residues and nucleic acids. If sufficient oxidative damage ensues, this will result in target-cell death (only within the illuminated area). Photosensitizers are commonly used in polymer chemistry in reactions such as photopolymerization, photocrosslinking, and photodegradation. Photosensitizers are also used to generate triplet-excited states in organic molecules with uses in photocatalysis, photon upconversion and photodynamic therapy.

"δ-Aminolevulinic acid (also dALA, δ-ALA, 5-ALA or 5-aminolevulinic acid)", an endogenous non-proteinogenic amino acid, is the first compound in the porphyrin synthesis pathway, the pathway that leads to heme in mammals, as well as chlorophyll in plants. In humans, 5-ALA is a precursor to heme. Biosynthesized 5-ALA undergoes series of transformations in the cytosol and finally gets converted to protoporphyrin IX inside the mitochondria. This protoporphyrin molecule chelates with iron in presence of enzyme ferrochelatase to produce heme. Cancer cells lack or have reduced ferrochelatase activity and this results in accumulation of protoporphyrin IX, a fluorescent substance that can easily be visualized. Excess heme is converted in macrophages to biliverdin and ferrous ions by the enzyme HO-1. Biliverdin formed further gets converted to bilirubin and carbon monoxide. As they are used here, the terms δ-Aminolevulinic acid, dALA, δ-ALA, 5-ALA, ALA or 5-aminolevulinic acid refer to ALA itself, precursors thereof, esters thereof and pharmaceutically acceptable salts of the same.

LEVULAN® KERASTICK® (LK-ALA) is a drug-device combination approved by USFDA for photodynamic therapy of Actinic Keratoses. LK-ALA comprises a composition of 5-aminolevulinic acid as photosensitizer and a blue light source—BLU-U®. Ameluz® is another drug-device combination approved by USFDA for photodynamic therapy of Actinic Keratoses and comprises a composition of 5-aminolevulinic acid and a red light source—RHODOLED®.

In one aspect, as shown in the non-limiting exemplary embodiment of FIG. 8, the present invention provides a method 800 of treating dermal neurofibroma comprising:

a. topically applying, at step 806, a pharmaceutical composition comprising a photosensitizer to the affected area of a patient,
b. incubating, at step 808, the affected area, and
c. irradiating, at step 810, the affected area with a light of suitable wavelength as per the photosensitizer used;

wherein the treatment is characterized by inhibiting the progression of tumor growth and/or reduction in tumor size and/or increased mortality rate of the neurofibroma cells.

One example of a treatment method for dermal neurofibroma, by photodynamic therapy with ALA is described. Essentially anhydrous ALA is admixed with the vehicle just prior to its use. The anhydrous ALA may be, for example, the hydrochloride salt of aminolevulinic acid (ALA), an endogenous 5-carbon aminoketone. In at least one embodiment, the ALA is contained in powdered form inside a first ampule. A second ampule contains a solution vehicle. The first and second ampules are contained inside a plastic applicator. The first and second ampules may be crushed, e.g., by applying finger pressure, or inside a device configured to exert pressure on the ampule. Once the ampules are crushed, the ALA formerly contained in the first ampule contacts the solution formerly contained in the second ampule, and dissolves in the solution vehicle. The applicator in which the ampules were provided may be shaken so as to disperse and dissolve the powdered ALA in the solution vehicle. Once combined, the resulting solution is applied to the patient within 2 hours of preparation.

In some embodiments, the ALA may be provided in a composition such as a ready-to-use solution or a reconstituted powder for solution, gel, cream or lotion formulation. In another embodiment, the composition comprises 5-aminolevulinic acid hydrochloride in an amount of about 10% to about 70% w/w based on the total weight of the composition, preferably from about 20% to about 50% w/w based on the total weight of the composition.

In one embodiment, the pharmaceutical composition comprises about 10% w/v to about 20% w/v of 5-aminolevulinic acid as photosensitizer. In a preferred embodiment, the pharmaceutical composition comprises 10% w/v of 5-aminolevulinic acid. In another preferred embodiment, the pharmaceutical composition comprises 20% w/v of 5-aminolevulinic acid.

The ALA admixture is topically applied to the affected area using a point applicator to control dispersion of the ALA admixture, in at least one embodiment, so as to achieve a substantially uniform wetting of the affected area with the ALA by contacting the ALA with the affected area. The term "substantial," or "substantially" as used herein, may refer to any value which lies within the range as defined by a variation of up to ±15 from the average value. However, in other embodiments, the ALA may be applied digitally (i.e., by first disposing the ALA on the gloved fingertips of a practitioner, who then dabs the ALA on the region to be treated), or with a tool such as a spatula.

In one embodiment, the invention may comprise an additional step of microneedling before and/or after topical application of the photosensitizer composition.

In one aspect, the present invention provides a method of treating dermal neurofibroma comprising:

a. topically applying a pharmaceutical composition comprising ALA to the affected area of a patient,
b. incubating the affected area, and
c. irradiating the affected area with a light of suitable wavelength;

wherein the treatment is characterized by inhibiting the progression of tumor growth.

In another aspect, the present invention provides a method of treating dermal neurofibroma comprising:

a. topically applying a pharmaceutical composition comprising ALA to the affected area of a patient,
b. incubating the affected area, and
c. irradiating the affected area with a light of suitable wavelength;

wherein the treatment is characterized by reduction in tumor size.

In another aspect, the present invention provides a method of treating dermal neurofibroma comprising:

a. topically applying a pharmaceutical composition comprising ALA to the affected area of a patient,
b. incubating the affected area, and
c. irradiating the affected area with a light of suitable wavelength;

wherein the treatment is characterized by increased mortality rate of the neurofibroma cells.

In one aspect, the present invention provides a method of treating dermal neurofibroma comprising:

a. topically applying a pharmaceutical composition comprising ALA to the affected area of a patient,
b. incubating the affected area, and
c. irradiating the affected area with a light of suitable wavelength;

wherein the treatment is characterized by inhibiting the progression of tumor growth and reduction in tumor size and increased mortality rate of the neurofibroma cells.

In one aspect, the present invention provides a method of treating dermal neurofibroma comprising:

a. topically applying a pharmaceutical composition comprising ALA to the affected area of a patient,
b. incubating the affected area, and
c. irradiating the affected area with a light of suitable wavelength;

wherein the treatment is characterized by inhibiting the progression of tumor growth and/or reduction in tumor size and/or increased mortality rate of the neurofibroma cells.

For effective treatment, it is desirable to have a power output that is uniform in intensity and color. Illuminators, such as those disclosed in U.S. Pat. Nos. 8,758,418; 8,216,289; 8,030,836; 7,723,910; 7,190,109; 6,709,446; 6,223,071 and International Published Patent Application No. WO 2017/066270, which are incorporated by reference in their entireties for the techniques, methods, compositions, and devices related to PDT and PD, are typically used to provide the proper uniformity of light for treatment purposes. These devices generally include a light source (e.g., a fluorescent tube or LED), coupling elements that direct, filter or otherwise conduct emitted light so that it arrives at its intended target in a usable form, and a control system that starts and stops the production of light when necessary. Preferably, the light source is LED.

In at least one embodiment, for the treatment of dermal neurofibroma, the light source preferably emits blue light having wavelengths at or above 400 nanometers (nm), for example, about 430 nm, about 420 nm or, for example, 417 nm. However, the light source may also emit visible light in other ranges of the spectrum, such as in the green and/or red ranges between 400 and 700 nm, for example, about 625 nm to 640 nm or, for example, 635 nm. For example, the light source may also emit light having wavelengths of 510 nm, 540 nm, 575 nm, 630 nm, or 635 nm. In addition, the light source may be configured to emit light continuously or the light source may be configured to flash the diodes on and off based on a predetermined interval. Furthermore, the light source may be configured such that only one wavelength of light (e.g., blue) is emitted. Alternatively, the light source may be configured such that two or more wavelengths of light are emitted from the arrays. For example, the light source may be configured to alternately emit blue light and red light for treatment purposes.

In one embodiment, the light used for irradiation of the affected area is selected from a group consisting of a blue light, a red light and a white light. In a preferred embodiment the light used is a blue light. In more preferred embodiment, the blue light used has a wavelength in the range of 410 nm to 485 nm. In one of the most preferred embodiments, the blue light used is of a wavelength of 417 nm+5 nm. In the most preferred embodiment, the blue light used is of 417+5 nm. The intensity of the light may be increased or decreased, and the treatment time may be reduced or increased in such a way that the total applied dose remains same.

In one embodiment of the present disclosure, blue light having a wavelength of approximately 417 nm is applied at an intensity of 10 mW/cm$^2$ for 1000 seconds to provide a dose of 10 J/cm$^2$. However, the intensity may be increased (for example, doubled) to 20 J/cm$^2$, to reduce the treatment time. For example, the intensity may be increased so as to reduce the treatment time by about one-half. Preferably, the blue light is applied for a period in the range of 5 to 15 minutes.

In another embodiment, the light used for irradiation of the affected area is a red light. In a preferred embodiment, the red light used at a radiant flux of 105 mW/cm$^2$ and a dose of 50 or 100 J/cm$^2$ has a wavelength in the range of 625 nm to 740 nm. In one of the most preferred embodiment, the red light used is of a wavelength 633+5 nm.

In one aspect, the present invention provides a method of treating dermal neurofibroma comprising:

a. topically applying a pharmaceutical composition comprising ALA to the affected area of a patient,
b. incubating the affected area, and
c. irradiating the affected area with red light;

wherein the treatment is characterized by inhibiting the progression of tumor growth.

In another aspect, the present invention provides a method of treating dermal neurofibroma comprising:

a. topically applying a pharmaceutical composition comprising ALA to the affected area of a patient,
b. incubating the affected area, and
c. irradiating the affected area with red light;

wherein the treatment is characterized by reduction in tumor size.

In another aspect, the present invention provides a method of treating dermal neurofibroma comprising:

a. topically applying a pharmaceutical composition comprising ALA to the affected area of a patient,
b. incubating the affected area, and
c. irradiating the affected area with red light;

wherein the treatment is characterized by increased mortality rate of the neurofibroma cells.

In one aspect, the present invention provides a method of treating dermal neurofibroma comprising:

a. topically applying a pharmaceutical composition comprising ALA to the affected area of a patient,
b. incubating the affected area, and
c. irradiating the affected area with red light;

wherein the treatment is characterized by inhibiting the progression of tumor growth and reduction in tumor size and increased mortality rate of the neurofibroma cells.

In one aspect, the present invention provides a method of treating dermal neurofibroma comprising:

a. topically applying a pharmaceutical composition comprising ALA to the affected area of a patient, b. incubating the affected area, and c. irradiating the affected area with red light;

wherein the treatment is characterized by inhibiting the progression of tumor growth and/or reduction in tumor size and/or increased mortality rate of the neurofibroma cells.

In another embodiment, the illuminator may irradiate the affected area with a uniform intensity red light for a prescribed period. In certain embodiments, the illuminator irradiates the affected area with a uniform intensity blue light for a first prescribed period and then irradiates the affected area with a uniform intensity red light for a second prescribed period. For example, in some embodiments, the illuminator is configured to irradiate the affected area with a uniform intensity blue light (e.g., 417 nm) at a low intensity (e.g., about 0.1 $J/cm^2$ to about 2 $J/cm^2$) to photobleach, for example, protoporphyrin IX (PpIX) present at the surface of the patient's skin, and irradiate the affected area with a uniform intensity red light (e.g., 635 nm) at a high intensity (e.g., about 30 $J/cm^2$ to about 150 $J/cm^2$) to activate PpIX present at deeper layers of the patient's skin, thus avoiding potential damage to the upper layers of the patient's skin.

Furthermore, since the total light dose ($J/cm^2$) is equal to irradiance ($W/cm^2$) multiplied by time (sec), an additional parameter to be controlled for delivery of the correct treatment light dose is exposure time. This may be accomplished by the timer, which can control the electrical power supplied to the light source appropriately, and which can be set by the physician. An adjustable illuminator may deliver an irradiance density of 20 $mW/cm^2$ for an exposure time of 500 seconds (8 min. 20 sec) to deliver a clinically acceptable light dose of 10 $J/cm^2$. In certain embodiments, a lower intensity may be used with a longer exposure time (e.g., 1,000 seconds of exposure time for a light dose of 10 $J/cm^2$). Alternatively, the illuminator may include higher power ranges, such as 30 $mW/cm^2$, over an exposure time resulting in a light dose of 10 $J/cm^2$. A selected light dose may also be administered by additionally or alternatively varying the irradiance density over treatment time. In the most preferred embodiment, the red light of 633 nm is applied for providing a dose of about 10 to 75 $J/cm^2$ in about 1.5 to 12 minutes. In one of the preferred embodiments, the red light is applied at an intensity of about 100 $mW/cm^2$ to provide a dose of about 50 $J/cm^2$.

The light source used for generating the light for irradiation of the affected area may be selected from a group consisting of an arc lamp, an incandescent light source (glowing filament), a fluorescent light source (glowing gas), a laser light source (coherent light), a red light source, a halogen laser light source, a blue light source and a light emitting diode (LED).

The treatment of dermal neurofibroma according to one of the preferred embodiments of the present invention may be characterized by increased mortality rate of neurofibroma cells. In another embodiment, the treatment may be characterized by inhibition of the progression of tumor growth. In yet another embodiment, the treatment may be characterized by reduction in tumor size. In some embodiments, the treatment may be characterized by a combination of one or more above such parameters. In a specific embodiment, the increased mortality rate of neurofibroma cells is determined by appearance or detection of increased DNA fragmentation by suitable analytical methods. One non-limiting example of such analytical method is TUNEL assay.

Referring again to FIG. 8, one of the embodiments, the invention may optionally comprise an additional step (at step 802) that is degreasing of the affected area, before topical application of the photosensitizer. In the same or another embodiment, the invention may also comprise an additional step (at step 804) of microneedling before and/or after topical application of the photosensitizer composition. Although FIG. 8 depicts microneedling prior to topical application of the photosensitizer, it may be performed after, or before and after, application.

In another aspect, the invention provides use of a pharmaceutical composition of 5-aminolevulinic acid for treatment of dermal neurofibroma using photodynamic therapy with a red light or a blue light, wherein the treatment is characterized by inhibiting the progression of tumor growth and/or reduction in tumor size and/or increased mortality rate of the neurofibroma cells.

Example 1

PART 1: Subject Population and Treatment

Four adult subjects were enrolled (2 males, 2 females) in part 1. Three tumor groups for each subject consisted of untreated negative controls, tumors treated with drug vehicle only, and ALA (Levulan® Kerastick® Topical Solution, Sun Pharma, Wilmington, MA, USA) treated tumors. Treated tumors were incubated with ALA or vehicle three hours (2 subjects) or overnight (2 subjects), then excised and subjected to fluorescence microscopy studies to measure mean fluorescence indicating PpIX conversion in tumors. Four adult subjects (2 males, 2 females) participated in part 1. Ages ranged from 39 to 67 yrs.

Inclusion criteria included adult patients aged 17 years or older with a NF1 diagnosis as classified by American Academy of Neurology and NIH Guidelines (Gutmann et al., Jama 1997; 278: 51-7), presence of superficial dermal neurofibromas those who were to undergo tumor excision as part of their standard care, the presence of cutaneous tumor with localization on the trunk or limbs only, and growth confirmation via direct measurement of the dermal neurofibromas, ruler and photo-volumetric method, and absence of any other malignancy.

Exclusion criteria included life expectancy less than 1 year, pregnancy, inability to consent, cutaneous photosensitivity to the wavelengths used to activate the PS, diagnosis of porphyria, allergy to ALA or any of the topical solution vehicle components, previous chemotherapy within 6 weeks of proposed PDT, and other concurrent tumor therapy.

Photosensitizer Uptake: Treated tumors were incubated with ALA or vehicle three hours (2 subjects) or overnight (2 subjects), then excised and subjected to fluorescence microscopy studies to measure mean fluorescence indicating PpIX conversion in tumors. Importantly, ALA delivery for the subjects undergoing overnight incubation was assisted using microneedling (Dermapen®, Salt Lake City, Utah) of the tumors. The tumors were degreased with alcohol, painted with ALA or vehicle, and microneedled using 1.5-2 mm depth setting until pinpoint bleeding was observed. During and immediately after microneedling, ALA or vehicle was reapplied. The primary outcome measure was the ratio of mean fluorescence intensity in tumors compared to adjacent normal tissue, as determined by confocal microscopy. PpIX signals were detected with excitation at 405 nm and emission with a 600 nm long pass filter.

Example 2

PART 2: Subject Population and Treatment

Nine adult subjects participated in part 2, four male and five female. Ages ranged from 39 to 69, with a median of 58. For each subject neurofibromalesions were selected for treatment with ALA (3-6 lesions) and vehicle (3-6 lesions) delivered with microneedling. Following an overnight (16-18 hrs.) incubation time, all treated neurofibromas were illuminated with red light at 633 nm and 105 mW/cm$^2$ (Omnilux Revive® LED illuminator, Photo Therapeutics, Montgomeryville, PA, USA). The dose escalation study included doses of 50, 100 or 200 J/cm$^2$. Each subject received one single treatment.

Study Design: This study followed a 3+3 Phase I trial design, subjects were treated starting at a dose level of 50 J/cm$^2$. Dose escalation was performed only after a minimum of three subjects had been evaluated at the current level. If dose-limiting toxicity (DLT) occurred in 1 of 3 subjects, 3 more subjects would be evaluated at that dose level. DLT was defined as pain during irradiation requiring cessation of the light treatment, or any serious cutaneous adverse events, such as erosions or blistering or crusting of the skin. If 0 of these 3 subjects experienced DLT, then the dose was escalated (only one DLT in six subjects). If DLT occurred in 1 of the additional 3 subjects, the mean tolerable dose (MTD) had been exceeded (two DLTs in six subjects) and 3 more subjects would be treated at the next lower dose (if only 3 subjects had been treated previously at that dose). If DLT was noted in 2 of 3 subjects at a given dose level, the MTh had been exceeded and 3 more subjects are treated at the next lower dose level (if only 3 subjects were treated previously at that dose). The MTD is defined as that dose level immediately below the dose level at which 2 subjects of a cohort (three or six subjects) experience DLT.

Protocol: Subjects were seen at 48 hrs. (day 2), and 2 to 4 (day 14-28) weeks after light treatment, for evaluation of cutaneous adverse events. At day 2, tumors were biopsied using a punch technique and subjected to light microscopy exam, TUNEL assay (DeadEnd™ Colorimetric TUNEL System, Promega, Madison, WI), and DAPI (4',6-diamidino-2-phenylindole) staining (ab228549, Abcam, Cambridge, MA). Additional follow-up visits for measurement of lesions were made at periods of 3 months up to one year. See FIG. 1 for a schematic of the study design. The primary outcome for this clinical study was MTD, as measured in the dose escalation using the DLT as defined above. A secondary outcome measured efficacy defined by change in lesion size. The area of the lesion was estimated at baseline and during follow-up visits by measuring the long and short axis of the lesion. Average growth rates were calculated and comparisons made between ALA-treated and placebo lesions within the same subject. The null hypothesis was that there would be no difference in the growth rates of ALA-treated lesions when paired with same-subject placebo lesions. The alternative hypothesis was there would be a difference in the ALA and placebo lesion growth rates.

Example 3

Quantification Method

Photosensitizer Uptake and Conversion: Tissue from excised tumors from the two subjects whose lesions were treated with topical ALA and incubated for 3 hrs. showed no fluorescence in the apparent tumor zones. There was a faint stain in the dermal regions that bleached quickly (not shown). The ALA infiltration was insufficient, and that modifications were necessary. Microneedled and ALA-treated tissue samples obtained after overnight incubation showed significant fluorescence compared to the adjacent normal tissue which was negative for fluorescence, indicating specific conversion of ALA to PpIX in the tumor but not in the normal tissue (FIG. 2*a*). Fluorescence values for PpIX positive tumor areas are given in Table 1. The average fluorescence value per area was 304±94 densitometry units/μm$^2$ (n=10). Using a one-sample t-test comparing the absolute value to an alternate expected value of zero, the results are significant with p<0.0001. Control and vehicle only tumors showed no visible fluorescence (FIG. 2*b*).

TABLE 1

Fluorescence values for protoporphyrin IX (PpIX) positive tumor areas.

| Sample | Positive area (μm$^2$) | Total densitometric value | Densitometry units/μm$^2$) |
|---|---|---|---|
| Sample # 1 - 5b | 5681 | 2856038 | 502.7 |
| Sample # 1 - 7b2 | 1786 | 491650 | 275.3 |
| Sample # 2 - 1b | 9936 | 1870257 | 188.2 |
| Sample # 2 - 5b-2 | 853 | 186321 | 218.4 |
| Sample # 3 - 4b | 28705 | 8142219 | 283.7 |
| Sample # 3 - 5b | 22779 | 4650898 | 204.2 |
| Sample # 5 - 4 | 50508 | 15091227 | 298.8 |
| Sample # 5 - 5 | 60482 | 22612588 | 373.9 |
| Sample # 7 - 4 | 22515 | 7558102 | 335.7 |
| Sample # 7 - 5 | 13367 | 4756842 | 355.9 |
| average | | | 304 ± 94 |

Clinical Evaluation: Red light at a radiant flux of 105 mW/cm$^2$ and a dose of 50 or 100 J/cm$^2$ resulted in marked erythema and edema around ALA-treated (n=24) but not placebo (n=20) lesions, which lasted for at least 48 hrs. (FIG. 3). There was no blister formation, erosion or crusting.

Dose Escalation: One subject in the initial cohort (50 J/cm$^2$) experienced pain requiring cessation of the light treatment. Due to this DLT, three more subjects were treated at this dose level, successfully, as well as the next dose level of 100 J/cm$^2$. No other serious cutaneous adverse events were experienced. However, red light treatment induced marked pain and discomfort in all ALA treated but not placebo lesions. Subjects could generally tolerate this level of pain, the increasing time of treatment became difficult to bear. Due to this marked pain, it was decided that the MTD would be set at 100 J/cm$^2$, and the highest dose level foregone, even though only one subject experienced DLT.

Light Microscopy: Light microscopy exam using standard hematoxylin & eosin staining showed a mixed infiltrate consisting of lymphocytes, neutrophils, and rare eosinophils in ALA-treated but not vehicle-treated tumors or normal adjacent tissue, indicating an inflammatory response in ALAPDT treated neurofibromas. (FIG. 4).

TUNEL Assay: Representative neurofibromas (three ALA-treated and one placebo treated) from five different subjects were evaluated for apoptotic cell death by TUNEL assay. FIG. 5 shows that there are more apoptotic cells in the ALA-treated neurofibromas samples compared to the vehicle-treated samples. FIG. 6 shows individual results for each of five subjects. FIG. 7 shows quantitatively that the average number of apoptotic cells per visual field among all TUNEL evaluated tumor samples was 42.5±19.9 for ALA-treated tumors and 1.1±1.4 for vehicle treated tumors (p=0.002).

Tumor Size: Treated tumors in five subjects were followed for measurement of size and clinical changes. Tumor sizes as measured at 2, 4 and 12 weeks after treatment did not show significant change. A non-significant trend for reduction in average lesion growth rates was observed in ALA-treated tumors (−0.13±0.22 $mm^2$/day post treatment) as compared to the vehicle treated tumors within the same subjects (Table 2).

TABLE 2

Lesion growth rates post PDT treatment.

| Subject # | Growth rate ALA ($mm^2$/day) | Growth rate placebo ($mm^2$/day) | Difference in growth rates |
|---|---|---|---|
| 12 | 0.028 (0.040) | 0.270 (0.073) | −0.239 |
| 13 | 0.097 (0.103) | 0 | 0.097 |
| 15 | 0.375 (00157) | 0.815 (0.208) | −0.440 |
| 16 | −0.024 (0.030) | 0.086 (0.089) | −0.110 |
| 17 | −0.073 (0.063) | −0.107 (0.288) | 0.034 |
| average | | | −0.132 (0.216) |

Discussion

The tumor-specific fluorescence, as a result of ALA-PpIX conversion by the tumors, was seen in excised NF1 lesions. The results seen in Part 1 of our study were deemed sufficient to move on to the Part 2 clinical trial phase. ALA-PDT treated NF lesions showed significant clinical responses compared to the vehicle treated lesions which demonstrated that the response was not due to the micro-needling procedure or the red light treatment alone. Edema and redness subsided by day 2 and post inflammatory hyperpigmentation lasted up to 3 months. ALA-treated tumors showed mixed inflammatory infiltrate and apoptotic cells. Light microscopy exam demonstrated a mixed inflammatory response and TUNEL assays confirmed significant apoptotic cell death in ALA-treated, but not vehicle-treated NF lesions, while adjacent normal skin and vehicle-treated tumors remained normal. These results clearly demonstrate the ALA-PDT has NF tumor specific effects.

The invention claimed is:

1. A method of treating dermal neurofibroma in a patient comprising:

a. topically applying a pharmaceutical composition comprising a photosensitizer to an affected area of the patient, b. microneedling the affected area before and/or after topical application of the photosensitizer, c. incubating the affected area, and d. irradiating the affected area with blue light;

wherein the treatment is effective to inhibit progression of neurofibroma tumor growth and/or achieve a reduction in neurofibroma tumor size and/or achieve an increased mortality rate of neurofibroma cells.

2. The method according to claim 1, wherein the pharmaceutical composition comprises 5-aminolevulinic acid as the photosensitizer.

3. The method according to claim 1, wherein the pharmaceutical composition comprises about 10% w/v to about 20% w/v of 5-aminolevulinic acid as the photosensitizer.

4. The method according to claim 1, wherein the wavelength of the blue light is in the range 410 nm to 485 nm.

5. The method according to claim 1, wherein the wavelength of the blue light is 417 nm±5 nm.

6. The method according to claim 1, wherein the blue light is applied at an intensity of 10 $mW/cm^2$ for 1000 seconds to provide a total applied dose of 10 $J/cm^2$.

7. The method according to claim 1, wherein the blue light is applied at an intensity of greater than 10 $mW/cm^2$ for less than 1000 seconds at a total applied dose of 10 $J/cm^2$.

8. The method according to claim 1, wherein the increased mortality rate of neurofibroma cells is determined by appearance or detection of increased DNA fragmentation.

9. The method according to claim 1, wherein the treatment further comprises a step of degreasing of the affected area before topical application of the photosensitizer.

10. The method according to claim 1, wherein the blue light is applied at a dose of 20 $J/cm^2$.

* * * * *